(12) United States Patent
Sato et al.

(10) Patent No.: US 8,875,703 B2
(45) Date of Patent: Nov. 4, 2014

(54) POWDER INHALER

(75) Inventors: Tetsuya Sato, Osaka (JP); Toru Nishibayashi, Osaka (JP); Yusuke Ogawa, Tokushima (JP); Takaaki Nakao, Tokushima (JP); Shintaro Adachi, Tokushima (JP)

(73) Assignees: Otsuka Pharmaceutical Co., Ltd., Tokyo (JP); Otsuka Techno Corporation, Tokushima (JP)

( * ) Notice: Subject to any disclaimer, the term of this patent is extended or adjusted under 35 U.S.C. 154(b) by 418 days.

(21) Appl. No.: 12/994,064

(22) PCT Filed: May 22, 2009

(86) PCT No.: PCT/JP2009/059463
§ 371 (c)(1),
(2), (4) Date: Dec. 7, 2010

(87) PCT Pub. No.: WO2009/142306
PCT Pub. Date: Nov. 26, 2009

(65) Prior Publication Data
US 2011/0067696 A1 Mar. 24, 2011

(30) Foreign Application Priority Data
May 23, 2008 (JP) ................................. 2008-135494

(51) Int. Cl.
*B05D 7/14* (2006.01)
*A61M 15/00* (2006.01)
*A61M 11/00* (2006.01)

(52) U.S. Cl.
CPC ....... *A61M 15/0065* (2013.01); *A61M 15/0026* (2013.01); *A61M 11/002* (2013.01); *A61M 2202/064* (2013.01); *A61M 15/0075* (2013.01)
USPC ................................. 128/203.15; 128/203.12

(58) Field of Classification Search
USPC .............. 128/203.12, 203.14–203.15, 203.19
See application file for complete search history.

(56) References Cited

U.S. PATENT DOCUMENTS 4,177,941 A * 12/1979 Leong ........................... 222/636
5,628,307 A * 5/1997 Clark et al. .............. 128/203.15
(Continued)

FOREIGN PATENT DOCUMENTS

CA 2 655 156 A1 1/2008
EP 1 504 781 A1 2/2005
(Continued)

OTHER PUBLICATIONS

Supplementary European Search Report dated Mar. 3, 2014 issued in corresponding European Patent Application No. 09 75 0668.7.

*Primary Examiner* — Rachel Young
(74) *Attorney, Agent, or Firm* — Sughrue Mion, PLLC

(57) ABSTRACT

A powder inhaler includes: a housing having a port; a storage member located in the housing for storing a powder medicament; and a medicament-delivery member provided in the housing. The medicament-delivery member includes at least one concave portion for receiving medicament, and is capable of taking, relative to the storage member, a receiving position wherein the concave portion receives a predetermined amount of powder medicament from the storage member, and an inhalation position wherein the powder medicament can be inhaled through the admission port; and a stirring member for stirring the powder medicament stored in the storage member. An operation button is provided in the housing and is capable of moving between the initial position and a depressed position, while the operation button reciprocates between the initial position and the depressed position, the concave portion in the medicament-delivery member moves from the receiving position to the inhalation position and the stirring member operates.

7 Claims, 27 Drawing Sheets

(56) References Cited

U.S. PATENT DOCUMENTS

Figure 1:
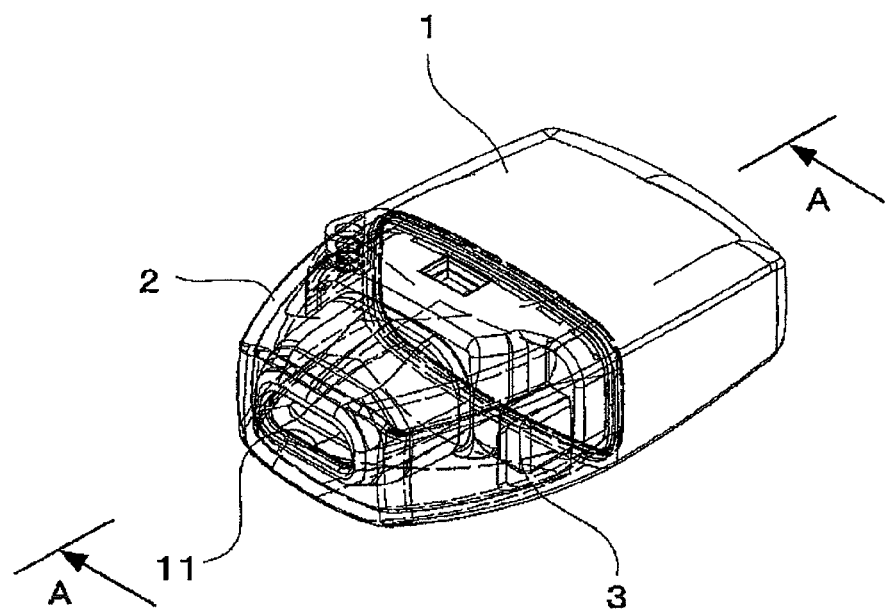
Figure 2:
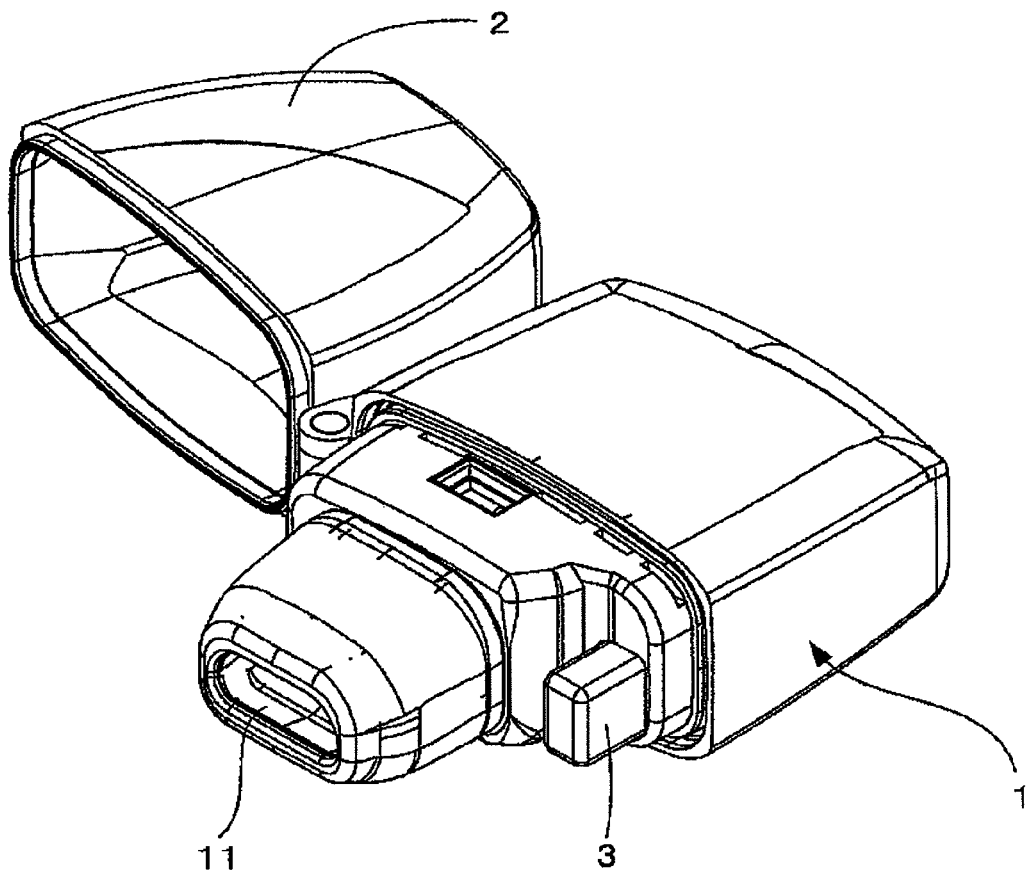

| | | |
|---|---|---|
| 6,029,661 A | 2/2000 | Whaley et al. |
| 6,257,232 B1* | 7/2001 | Andersson et al. ...... 128/203.15 |
| 6,886,560 B1* | 5/2005 | Seppala .................. 128/203.15 |
| 7,611,078 B2 | 11/2009 | Zaima et al. |
| 2002/0158150 A1 | 10/2002 | Matsugi et al. |
| 2003/0136406 A1* | 7/2003 | Seppala .................. 128/203.15 |
| 2004/0123865 A1* | 7/2004 | Haikarainen et al. .... 128/203.15 |
| 2004/0237276 A1 | 12/2004 | Zaima et al. |
| 2009/0205656 A1 | 8/2009 | Nishibayashi et al. |

FOREIGN PATENT DOCUMENTS

| | | |
|---|---|---|
| WO | 00/64518 A1 | 11/2000 |
| WO | 2004/007007 A1 | 1/2004 |
| WO | 2008/001744 A1 | 1/2008 |

* cited by examiner (a)

(b) (c)

(d) (e)

(a)

(b)

(a)

(b)

(a)

(b)

POWDER INHALER

This application is a National Stage of Application No. PCT/JP2009/059463 filed May 22, 2009, claiming priority based on Japanese Patent Application No. 2008-135494 filed May 23, 2008, the contents of all of which are incorporated herein by reference in their entirety.

TECHNICAL FIELD

The present invention relates to a powder inhaler capable of administering a powder medicament to a patient.

BACKGROUND ART

One example of this type of powder inhaler is disclosed in PTL 1. The powder inhaler is so structured that a patient may inhale the stored powder medicament through a mouthpiece. Specifically, when the patient depresses the operation button of the inhaler, a metered dose powder medicament is disposed to the inhalation position, and, in this condition, the patient can take the metered dose of powder medicament by inhaling air while holding the mouthpiece with his/her mouth.

CITATION LIST

Patent Literature

PTL 1: WO 2008/1744

SUMMARY OF INVENTION

Technical Problem

The powder medicament administered using the above-mentioned powder inhaler has poor fluidity or is easily solidified. Therefore, it has to be shaken before use, a troublesome operation for the patient.

An object of the present invention is to solve the above problem, and to provide a powder inhaler that is highly convenient and operable in an efficient manner, without requiring shaking before use.

Solution to Problem

The objective of the powder inhaler of the present invention is to solve the above problem. The powder inhaler includes a housing having an admission port; a storage member provided in the housing for storing a powder medicament; and a medicament-delivery member provided in the housing. The medicament-delivery member comprises at least one concave portion for receiving a predetermined amount of powder medicament, wherein the at least one concave portion is capable of taking, relative to the storage member, a receiving position in which the concave portion receives a predetermined amount of powder medicament from the storage member, and an inhalation position in which the powder medicament can be inhaled through the admission port. The powder inhaler further comprises a stirring member provided in the storage member for stirring the powder medicament stored in the storage member; and an operation button provided in the housing and being capable of moving between the initial position and depressed position. While the operation button reciprocates between the initial position and the depressed position, the concave portion in the medicament-delivery member moves from the receiving position to the inhalation position and the stirring member operates.

In the powder inhaler having such a structure, the housing is provided with a stirring member for stirring the powder medicament, and an operation button that can relatively transfer the medicament to the location where the patient can inhale the medicament. The powder inhaler is so structured that the stirring member is concurrently operated when the operation button is depressed and returns to the initial position. This structure allows the stored medicament to be stirred before inhalation, preventing the medicament form being coagulated. As a result, an accurate amount of the medicament can be stored in the concave portion, and the medicament can be reliably located at the inhalation position. The medicament-delivery member is movable relative to the storage member. In other words, either the medicament-delivery member or the storage member may be transferred, as long as the concave portion can move between the receiving position and the inhalation position during this relative movement.

The operation button may be structured as below. Specifically, the stirring member rotates when the operation button is shifted from the initial position to the depressed position, and the concave portion of the medicament-delivery member moves from the receiving position to the inhalation position when the operation button is shifted from the depressed position to the initial position. This allows the medicament to be mixed before being transferred to the inhalation position, and therefore blockage caused by the medicament can be reliably prevented. It is also possible to employ a structure wherein the stirring member operates, in preparation for the subsequent step, after the medicament is placed in the inhalation position.

In the inhaler, there are several methods to discharge the predetermined amount of medicament from the storage member. One example thereof is described below. Specifically, an exhaust port for discharging the powder medicament is formed in the storage member, and the region including the concave portion of the medicament-delivery member is formed so as to cover the exhaust port at the receiving position. In this structure, while the concave portion moves relatively from the receiving position to the inhalation position, the inner wall of the exhaust port removes the powder medicament that overflows from the concave portion.

In this structure, the powder medicament that overflows from the concave portion is removed; therefore, the concave portion accommodates only the predetermined amount of medicament. Because the thus-stored medicament is shifted to the inhalation position, the accurately measured amount of the medicament can be taken at every dosage.

In this case, a protrusion projecting toward the exhaust port can be provided on the medicament-delivery member in a stream lower than the concave portion in the rotation direction. This structure allows the protrusion to push the medicament stored in the exhaust port in the rotation direction, attributable to the movement of the medicament-delivery member relative to the storage member. This allows for easy storage of the medicament in the concave portion. There is no limitation to the shape and the number of the protrusion. For example, the protrusion may be formed of at least one cubical protrusion piece.

The stirring member may take various forms. For example, the stirring member may be formed of a rotational shaft and a plurality of impellers radially extending from the rotational shaft. In this case, the powder medicament can be mixed by the rotation of the impellers.

When the stirring member is formed of the rotational shaft and a plurality of impellers radially extending from the rotational shaft, it is preferable that at least one of the impellers move in the region corresponding to the exhaust port. This makes the impellers move in the vicinity of the exhaust port so that the powder medicament can be lead to the exhaust port by the impellers. This allows the powder medicament to be reliably supplied into the concave portion of the medicament-delivery member. The movement range of the impellers may be within that corresponding to the exhaust port. Alternatively, the impellers may pass over the exhaust port from outside the region corresponding to the exhaust port.

The medicament-delivery member can move relative to the storage member using various mechanisms. For example, it is possible to structure the medicament-delivery member to move between the receiving position and the inhalation position while reciprocating relative to the storage member. In this case, the medicament-delivery member can rotate while maintaining the reciprocating movement. Alternatively, the medicament-delivery member may be structured so as to move between the receiving position and the inhalation position while rotating in one direction relative to the storage member. In this case, it is possible to form a plurality of concave portions and make the medicament-delivery member move in the direction from the receiving position to the inhalation position. If the protrusion is provided on the medicament-delivery member, the protrusion can be designed to be retracted so that the protrusion does not interfere with the inner wall of the exhaust port, the storage member, or other members.

Advantageous Effects of Invention

The present invention can omit the shaking operation to loosen the blockage of the powder medicament before inhalation, thus improving its operability.

BRIEF DESCRIPTION OF DRAWINGS

FIG. 1 is a perspective view showing a powder inhaler according to the first embodiment of the present invention.

FIG. 2 is a perspective view of the powder inhaler of FIG. 1 when the cap is opened.

FIG. 3 is a cross-sectional view of FIG. 1 taken along the line A-A.

FIG. 4 is a partial perspective view of the powder inhaler according to the first embodiment of the present invention.

FIG. 5 is a plan view of FIG. 4 and an explanatory view of its operation.

FIG. 6 is a side elevational view of FIG. 4 illustrating the internal structure of the housing.

FIG. 7 is a partial cutaway perspective view of the storage member according to the first embodiment of the present invention.

FIG. 8 is a partial cutaway perspective view of the storage member according to the first embodiment of the present invention.

FIG. 9 is a perspective view of the storage member according to the first embodiment of the present invention.

FIG. 10 is a perspective view of the storage member according to the first embodiment of the present invention.

FIG. 11 is a partial cutaway perspective view of the storage member according to the first embodiment of the present invention.

FIG. 12 is a plan view of the storage member and medicament-delivery member according to the first embodiment of the present invention.

FIG. 13 is a sectional view imagining the flow of the medicament according to the first embodiment of the present invention.

FIG. 14 is a plan view of the reciprocal rotation mechanism seen from below the medicament-delivery member according to the first embodiment of the present invention.

FIG. 15 is an explanatory view of the reciprocal rotation of the medicament-delivery member according to the first embodiment of the present invention.

FIG. 16 is an explanatory view of the reciprocal rotation of the medicament-delivery member according to the first embodiment of the present invention.

FIG. 17 is an explanatory view of the reciprocal rotation of the medicament-delivery member according to the first embodiment of the present invention.

FIG. 18 is a perspective view showing the inner structure of powder inhaler according to the second embodiment of the present invention.

FIG. 19 is a perspective exploded view of the powder inhaler shown in FIG. 18.

FIG. 20 is a partial cutaway perspective view of the storage member shown in FIG. 18.

FIG. 21 is a plan view of FIG. 20.

FIG. 22 is a side view of FIG. 21.

FIG. 23 is a perspective view of FIG. 21.

FIG. 24 is another plan view showing the inner structure of the powder inhaler according to the second embodiment of the present invention.

FIG. 25 is a side view of FIG. 24.

FIG. 26 is another plan view showing the inner structure of the powder inhaler according to the second embodiment of the present invention.

FIG. 27 is a side view of FIG. 26.

DESCRIPTION OF EMBODIMENTS

First Embodiment

First embodiment of the powder inhaler of the present invention is explained below with reference to the drawings. FIG. 1 is a perspective view of the powder inhaler. FIG. 2 is a perspective view illustrating the powder inhaler of FIG. 1 when the cap is opened.

As shown in FIGS. 1 and 2, the powder inhaler of the present embodiment is formed into a thin rectangular parallelepiped shape, provided with a housing 1 having a mouthpiece (admission port) 11 at one end, and a transparent cap 2 covering the mouthpiece 11. The cap 2 is pivoted relative to the housing 1. Specifically, the cap 2 is pivoted between the initial position wherein the cap 2 covers the mouthpiece 11 as shown in FIG. 1, and the inhalation position wherein the mouthpiece 11 is exposed as shown in FIG. 2, so that a patient can hold it with his/her mouth. In the housing 1, an operation button 3 is provided in the portion where covered with the cap 2.

The internal structure of this powder inhaler is explained below. The suction channel of the powder medicament is explained with reference to FIG. 3. FIG. 3 is a cross-sectional view taken along the line A-A in FIG. 1.

As shown in the figures, in this powder inhaler, a powder medicament is stored in a circular cup-like storage member 4 provided in a housing 1. The powder medicament is discharged from an exhaust port 41 (see FIGS. 7 to 11) that is formed in the bottom of the storage member 4, and then transferred to an inhalation position by a medicament-delivery member 5 that is provided below the exhaust port 41. The inhalation position locates in a flow channel S in the housing 1 that communicably opens to the mouthpiece 11. In this structure, when the patient breaths in while holding the mouthpiece 11 with his/her mouth, the powder medicament passes through the flow channel S and then is inhaled by the patient.

Figure 4:
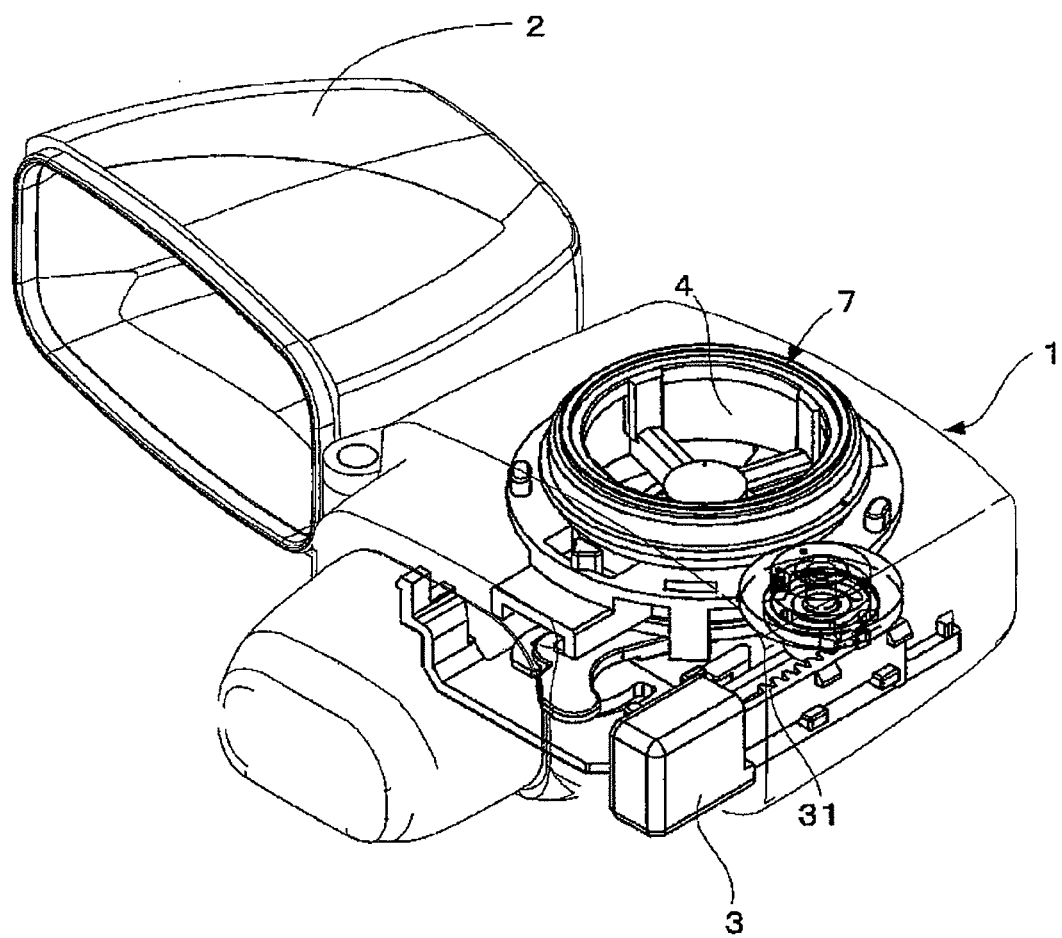
Figure 5:
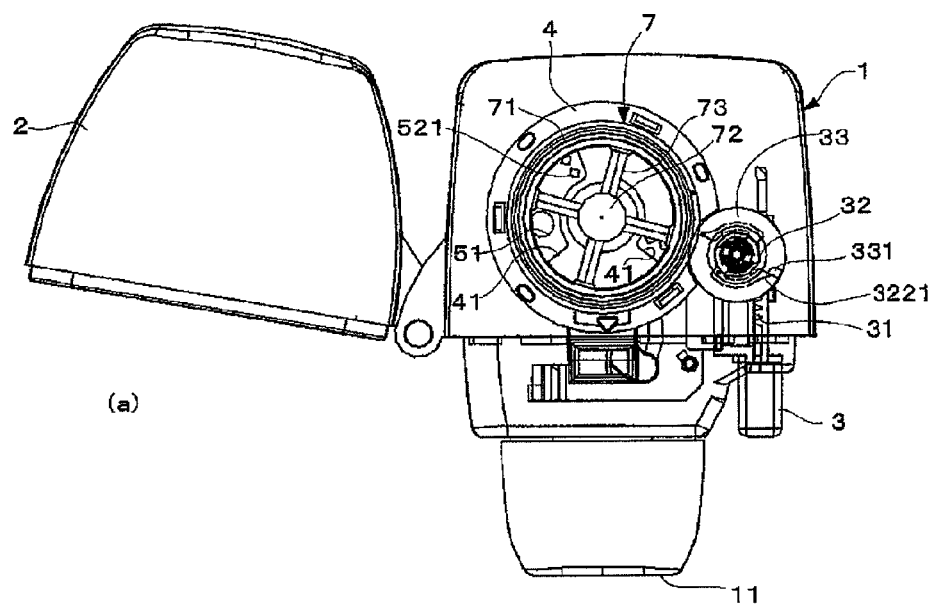
Figure 5:
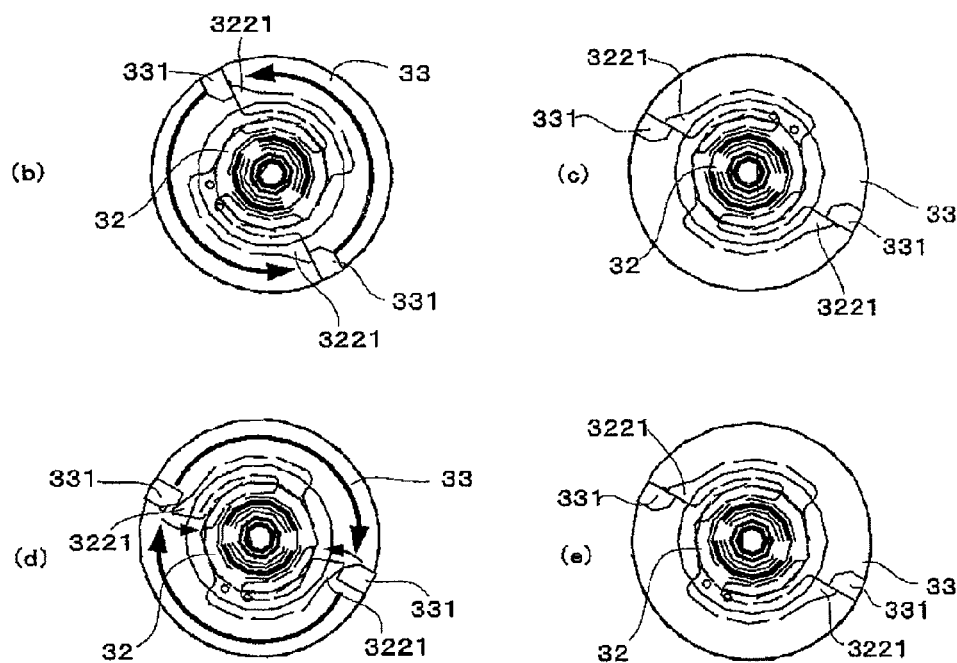
Figure 6:
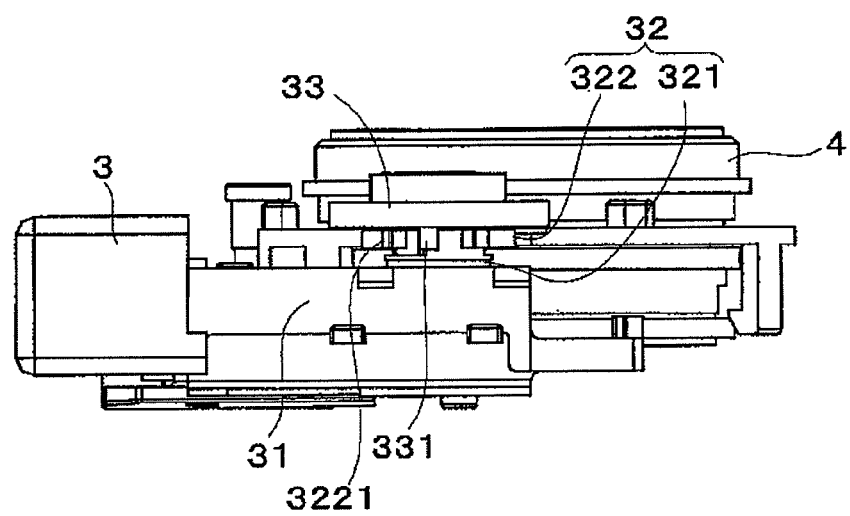
Figure 7:
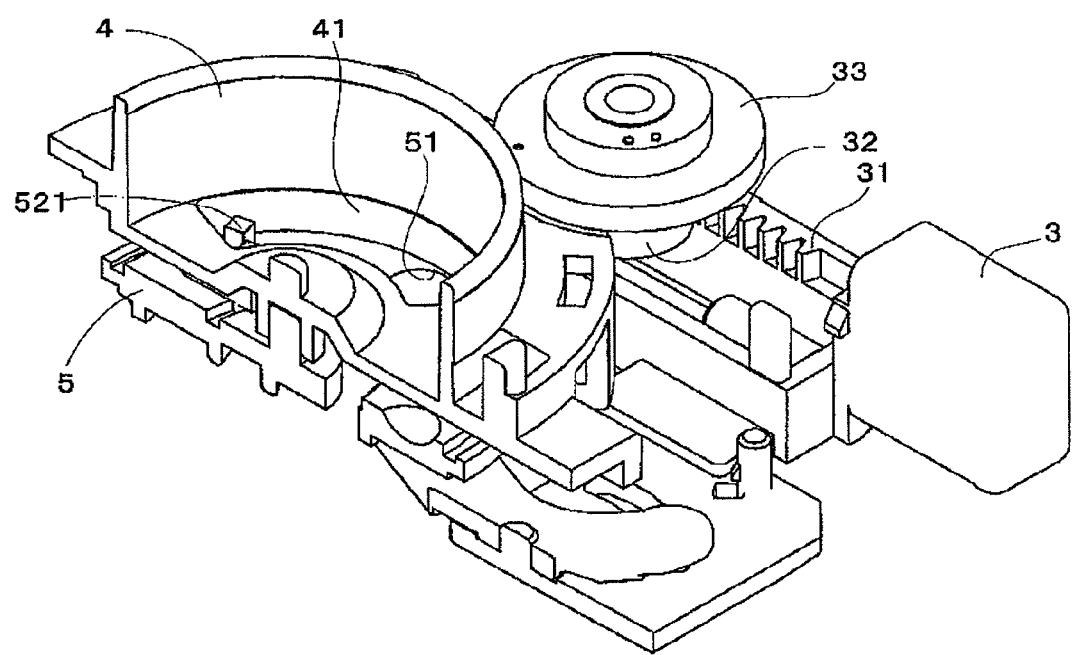

The structures of the storage member 4 and the medicament-delivery member 5 are explained below with reference to FIGS. 4 to 6. FIG. 4 is a partial perspective view of the powder inhaler. FIG. 5(a) is a plan view of FIG. 4, and FIGS. 5(b) to 5(e) illustrate the operation thereof. FIG. 6 is a side elevational view of FIG. 4 illustrating the internal structure of the housing.

As shown in FIGS. 4 to 6, the circular stirring member 7 is rotatably inserted in the above-explained storage member 4. The stirring member 7 is a means for stirring the powder medicament. The stirring member 7 is provided with an annular frame 71 rotatably engaged in the circumference of the storage member 4, and a rotational shaft 72 that is rotatably supported on the center of the bottom of the storage member 4, wherein these components are connected to each other by four stick-like impellers 73. The four impellers 73 radially extend from the rotational shaft 72 to be connected to the annular frame 71. A gear is formed on the peripheral surface of the annular frame 71, so that the stirring member 7 rotates when the operation button 3 is depressed. The operation button 3 is explained in detail below.

The operation button 3 is formed into a stick-like shape, energized with the spring (not shown) disposed in the housing 1, and a portion of the operation button 3 protrudes from the side surface of the mouthpiece 11 by the spring. The operation button 3 is provided with a rack 31 in the portion located in the housing 1, wherein the rack 31 meshes with a first gear 32. A second gear 33 is rotatably provided coaxially with the first gear 32, and the second gear 33 meshes with the gear of the annular frame 71. To be more specific, as shown in FIG. 6, the first gear 32 is formed of a gearing member 321, which meshes with the rack 31 of the operation button 3, and a circular engaging part 322, which coaxially connects to the gearing member 321 and meshes with the second gear 33. As shown in FIG. 5(a), the engaging part 322 has two engagement pieces 3221 placed opposing each other on the outer periphery. The engagement pieces 3221 can elastically deform and project in the radial direction. The second gear 33 is provided with two uniformly formed protrusions 331 that project toward the first gear 32. The protrusions 331 can engage with the above-described engagement pieces 3221 of the engaging part 322 in the first gear 32.

In this structure, the stirring member 7 operates as described below. Specifically, when the operation button 3 is depressed against the spring, the first gear 32 rotates due to the engagement with the rack 31. In this case, as shown in FIG. 5(b) and FIG. 5(c), due to the rotation of the first gear 32, each protrusion 331 is pushed toward the circumferential direction by each engagement piece 3221, and thereby the second gear 33 rotates together with each protrusion 331. This makes the stirring member 7 that engages with the second gear 33 rotate in the storage member 4. In contrast, when the operation button 3 is returned from the depressed position to the initial position by the force of the spring, the first gear 32 rotates in the opposite direction. However, in this case, because each protrusion 331 does not come in contact with each engagement piece 3221, the second gear 33 does not rotate. As shown in FIG. 5(d), when the first gear 32 rotates in the opposite direction, i.e., returning to the initial position, each protrusion 331 comes in contact with the other engagement piece 3221. However, when the counter-rotation progresses, each engagement piece 3221 is pressed inward in the radial direction by each protrusion 331. As a result, each protrusion 331 passes over each elastically deformable engagement piece 3221 from the outward in a radial direction so that the protrusion 331 is located at the position as shown in FIG. 5(e). This location is then defined as the initial position, and when the operation button 3 is depressed again, each protrusion 331 is pressed by each engagement piece 3221, rotating the second gear 33.

While the operation button 3 is being operated in such a manner as described above, the stirring member 7 rotates about 90° only in one direction. Because of the rotation of the stirring member 7, the four impellers 73 stir and mix the powder medicament in the storage member 4 so that the cluster thereof can be loosened. Additionally, although a drawing is omitted here, the second gear 33 engages with a gear of a counter. The counter counts the number of times the operation button 3 is depressed. The counter is so structured that the number of the counter decreases by one every time the second gear 33 rotates the predetermined angle. The number of the counter can be observed from outside the housing. The mechanism by which the stirring member 7 is rotated in one direction is not limited to that described above, and may be modified in various ways. Each rotation angle of the stirring member 7 is not limited to 90°, and may be suitably selected depending on the type of the medicament. In this case, the rotation angle can be adjusted depending on the speed-reducing ratio of the gears 32 and 33, the length of the stroke of the operation button 3, etc.

Subsequently, the supply of the medicament from the storage member into the flow channel is explained with reference to FIGS. 7 to 13. FIGS. 7 to 11 are perspective views including at least part of the storage member, FIG. 12(a) is a plan view of the internal structure of the housing, FIG. 12(b) is a plan view of the medicament-delivery member, and FIG. 13 is a sectional view imagining the flow of the medicament.

Figure 8:
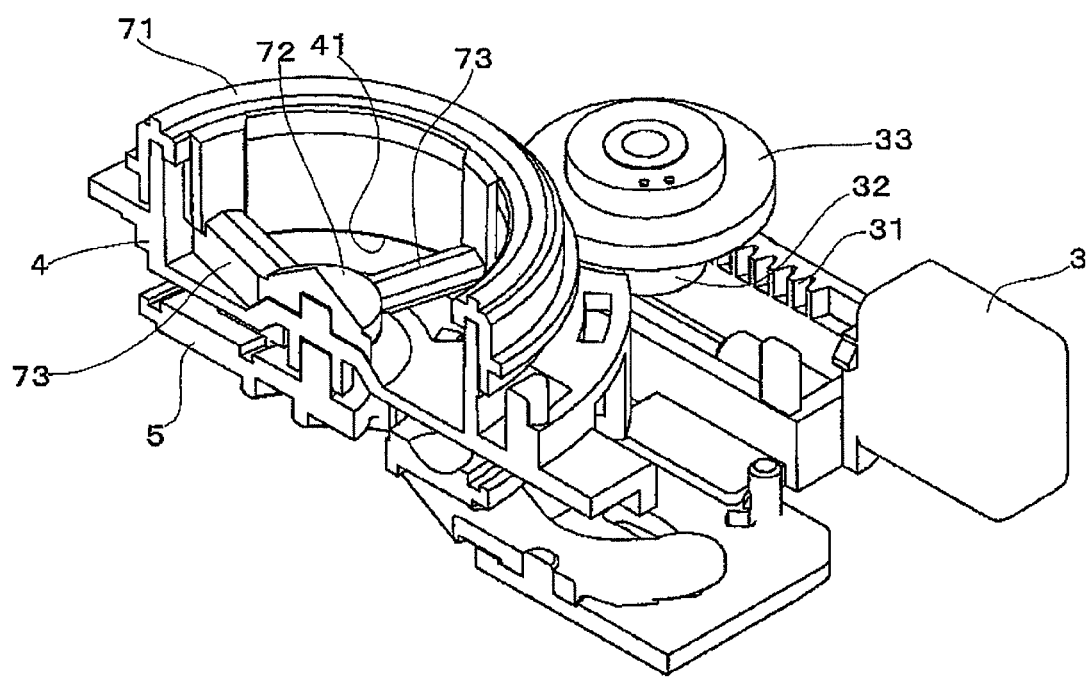
Figure 9:
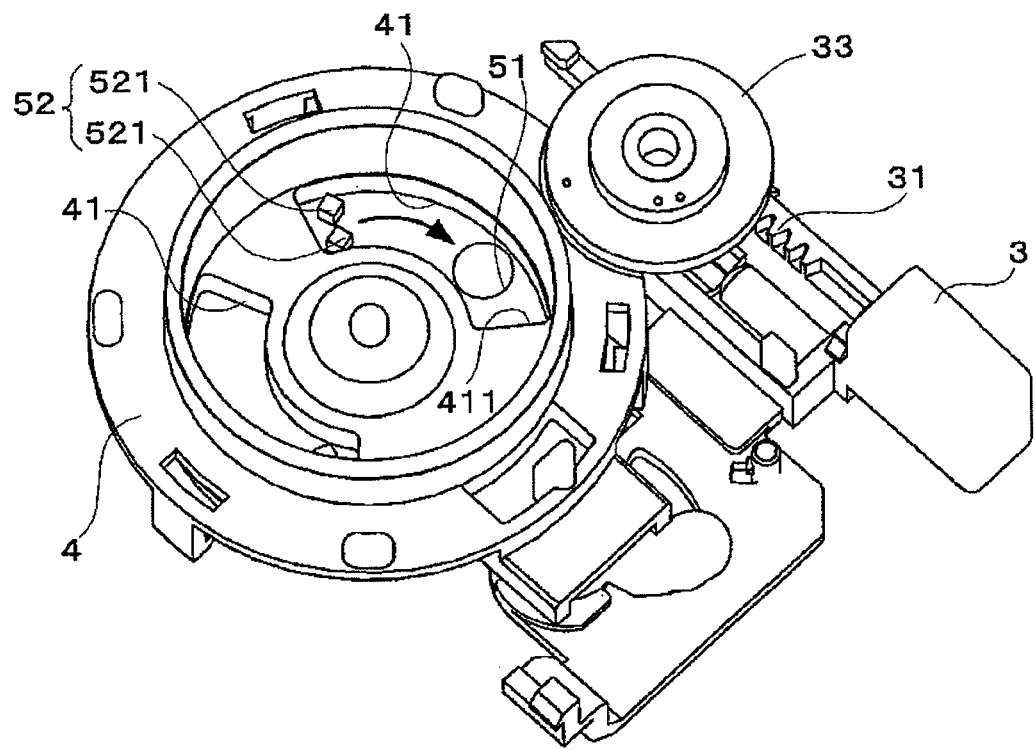
Figure 10:
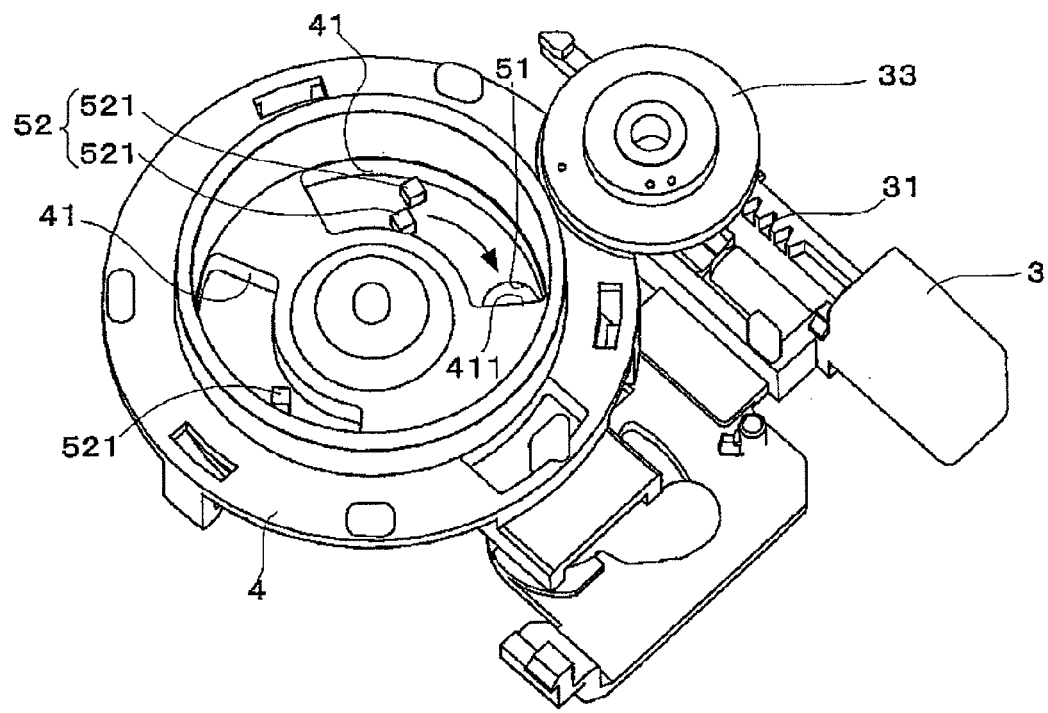
Figure 11:
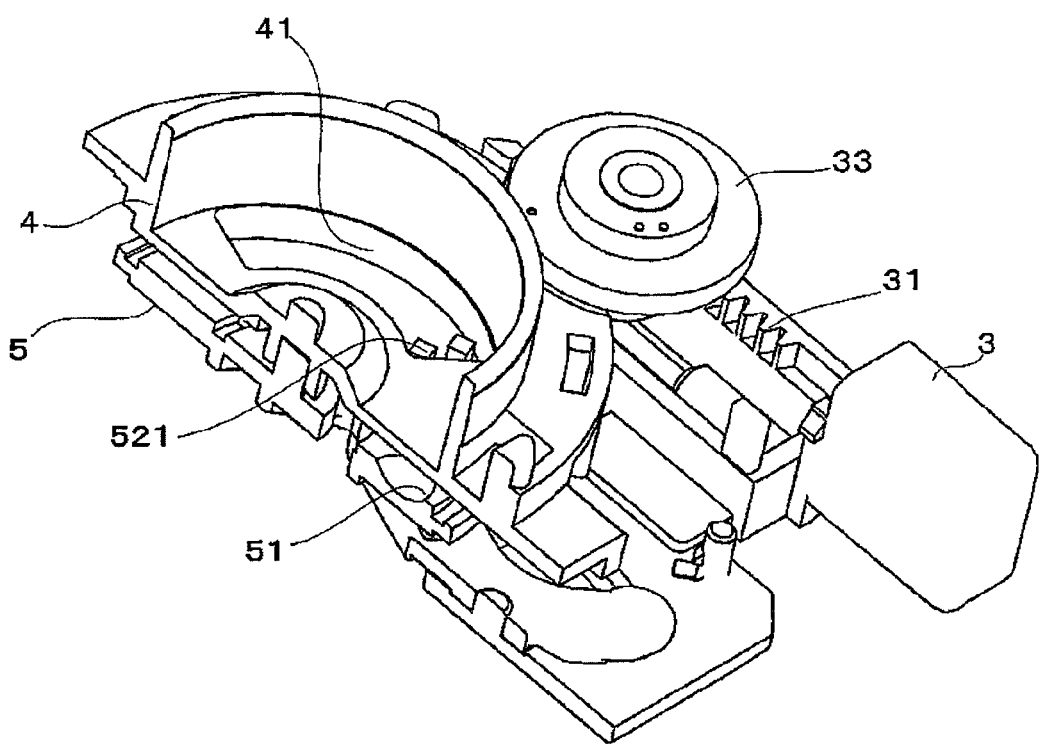
Figure 12:
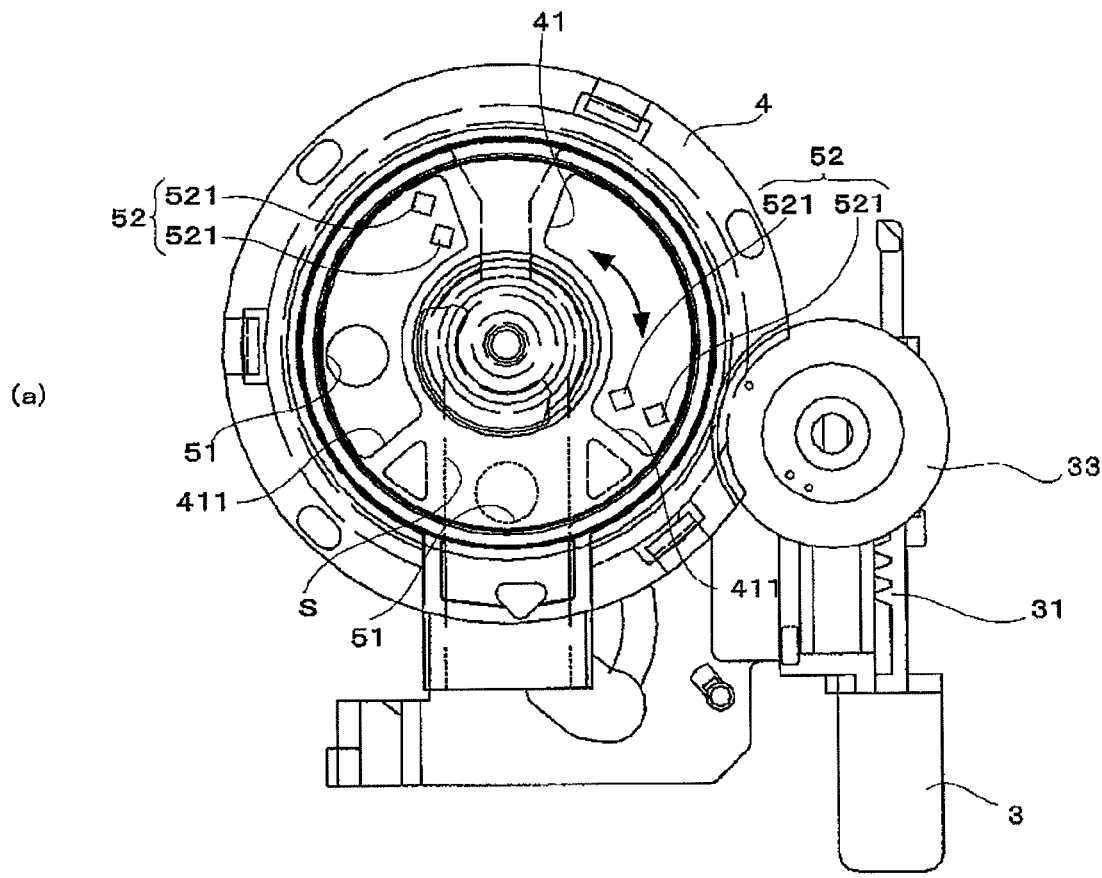
Figure 12:
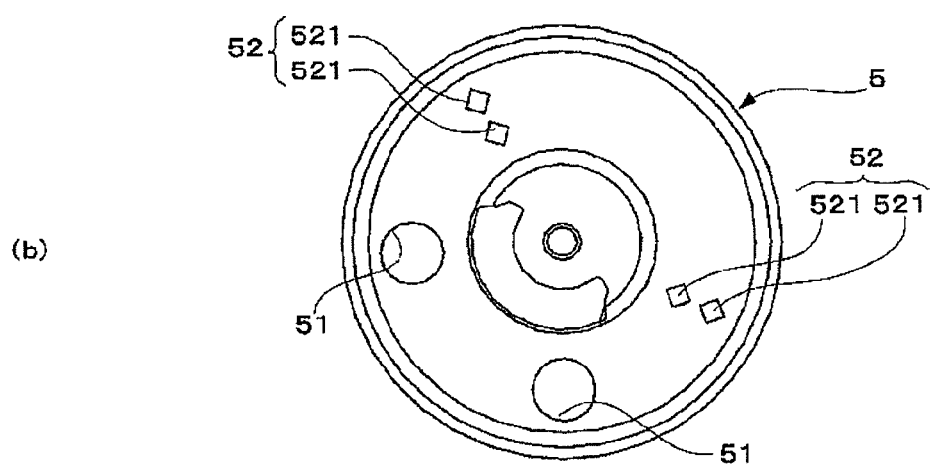
Figure 13:
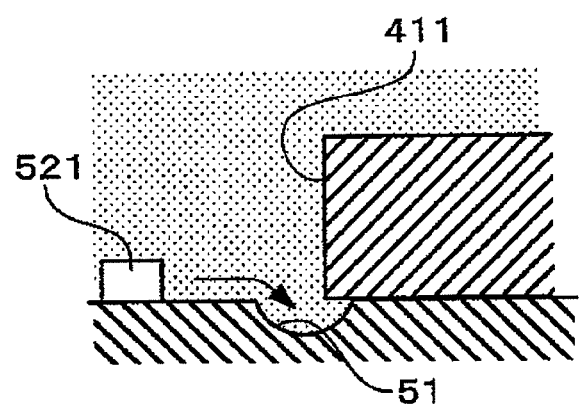

As shown in FIGS. 7 to 12, in the bottom surface of the storage member 4, two circular exhaust ports 41 are formed having the center of the bottom surface in between (see FIG. 12). Each of the exhaust ports 41 is formed to extend in the circumferential direction about 90°. As shown in FIG. 8, at least one impeller 73 of the above-described stirring member 7 moves above the exhaust port 41, so as to drop the powder medicament in the exhaust port 41 by the rotation of the impeller 73. A circular medicament-delivery member 5 is placed below the storage member 4 so as to cover the exhaust port 41. The medicament-delivery member is arranged coaxially with the storage member 4 and reciprocally rotates. The mechanism for the reciprocal rotation is described later.

As shown in FIGS. 11 and 12, in the medicament-delivery member 5, two hemispherical concave portions 51 are formed in the region that can be observed from the exhaust port 41. Each concave portion 51 has a volume for measuring a necessary dosage of the powder medicament for a single inhalation for a patient. The concave portions 51 are located about 90° away from each other along the circumferential direction. A protrusion 52 for pushing the powder medicament outward is formed at each location about 45° away from each concave portion 51 along the circumferential direction. The two protrusions 52 are located having the center of the medicament-delivery member 5 between them. Each protrusion 52 is formed of two adjacent protrusion pieces 521 (see FIGS. 9 and 10) and each protrusion piece is cubically shaped. Each protrusion piece 521 is disposed so that its corner faces the circumferential direction with a small space in the radial direction from each other. When the medicament-delivery member 5 rotates, the concave portion 51 and the protrusion 52 having such a structure rotate along the exhaust port 41 in such a manner that the concave portion 51 and the protrusion 52 face the inner space of the storage member 4 through the exhaust port 41. In this case, the protrusion 52 continuously projects toward the inside of the exhaust port 41 before and after the rotation. The concave portion 51 is exposed from the exhaust port 41 at the medicament-receiving position shown in FIG. 9; however, when the rotation of the medicament-delivery member 5 progresses as shown in FIG. 10 and FIG. 11, it passes over the exhaust port 41 and locates below the bottom of the storage member 4. This position is referred to as the inhalation position from which a patient can inhale the powder medicament.

The spatial relationship between the medicament-delivery member 5 and the storage member 4 is explained below in further detail. In the condition shown in FIG. 10, the concave portion 51 moves from the position where it is exposed from the exhaust port 41 to downward in the bottom of the storage member 4. In this condition, the surface of the medicament-delivery member 5 is in contact with the lower end of the side wall 411 of the exhaust port 41. Therefore, when the medicament-delivery member 5 rotates, the lower end of the side wall 411 of the exhaust port 41 removes the powder medicament on the surface of the medicament-delivery member 5. The powder medicament overflowed from the concave portion 51 is removed, so that the concave portion 51 moves, while holding the metered dose powder medicament, toward the downward of the storage member 4, i.e., to the inhalation position. In this structure, the protrusion pieces 521 push the powder medicament in the rotation direction due to the rotation, so that the powder medicament is reliably mixed and placed in the concave portion 51 as shown in FIG. 13. A space is formed between the two protrusion pieces 521 so that the medicament can easily pass through the space and in a uniform manner without being overbalanced on one side. By making the corner of the protrusion piece 521 face the circumferential direction, the medicament can pass smoothly through the side surfaces of the protrusion pieces 521 without being blocked by the protrusion 52.

Two concave portions 51 are formed in the medicament-delivery member 5. While the operation button 3 is returning from the depressed position to the initial position, one of the two concave portions 51 moves from the medicament-receiving position that is exposed from the exhaust port 41 to the inhalation position. During this operation, the other concave portion 51 moves from the inhalation position to the receiving position, so as to be ready for the subsequence medicament supply when the operation button 3 is depressed.

Figure 14:
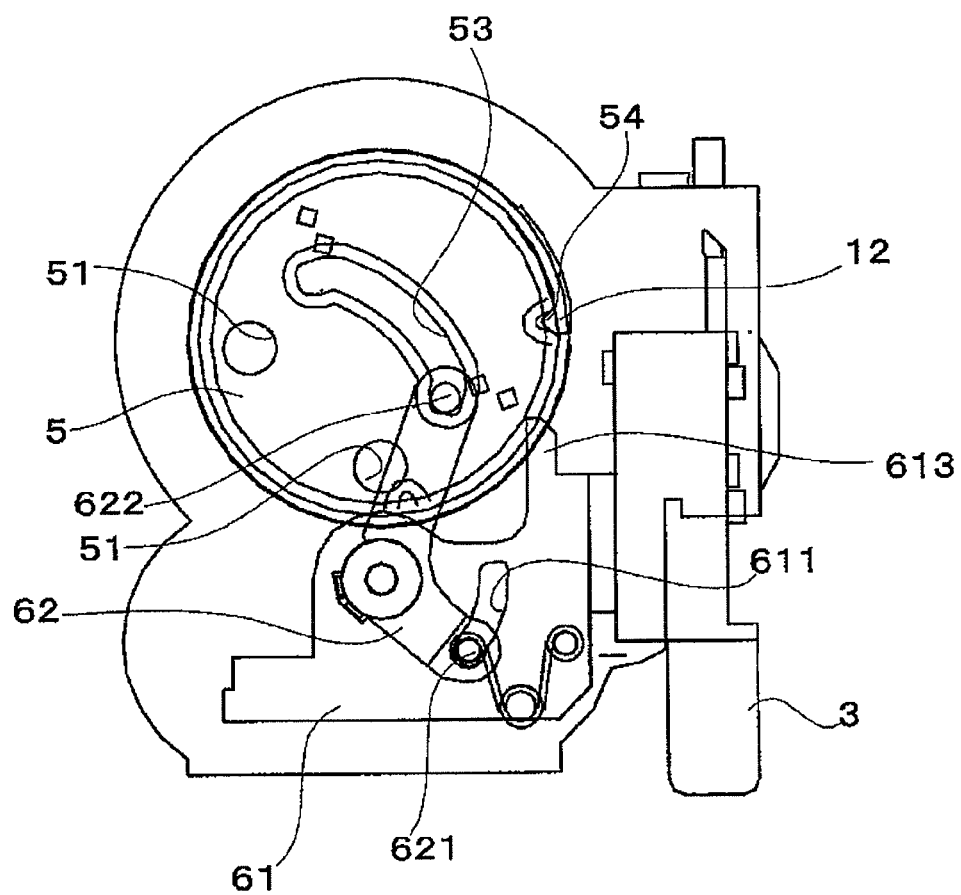
Figure 15:
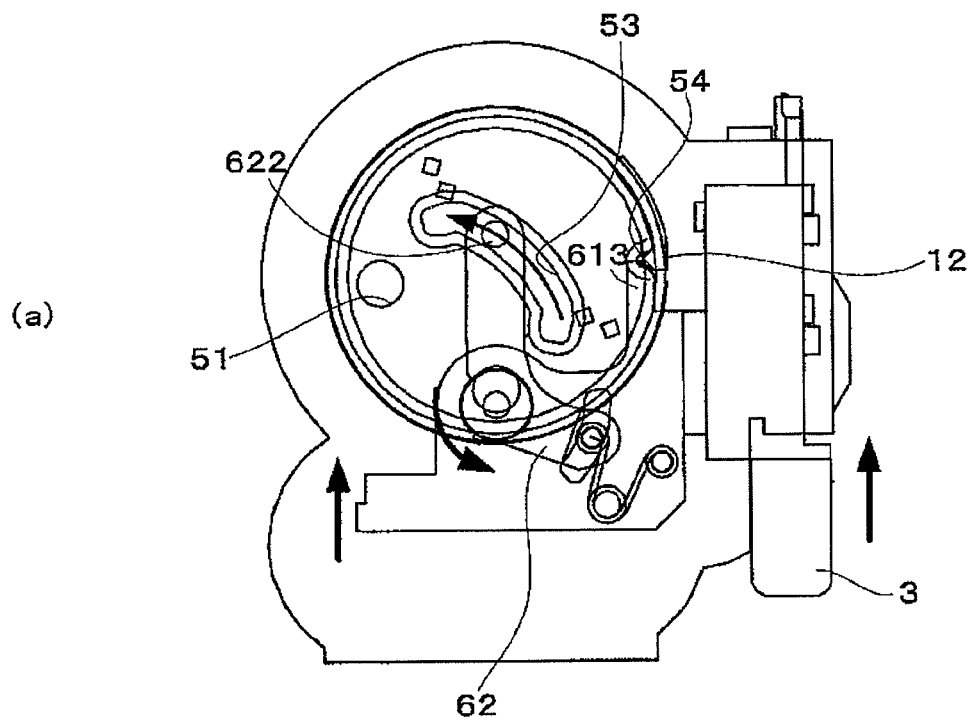
Figure 15:
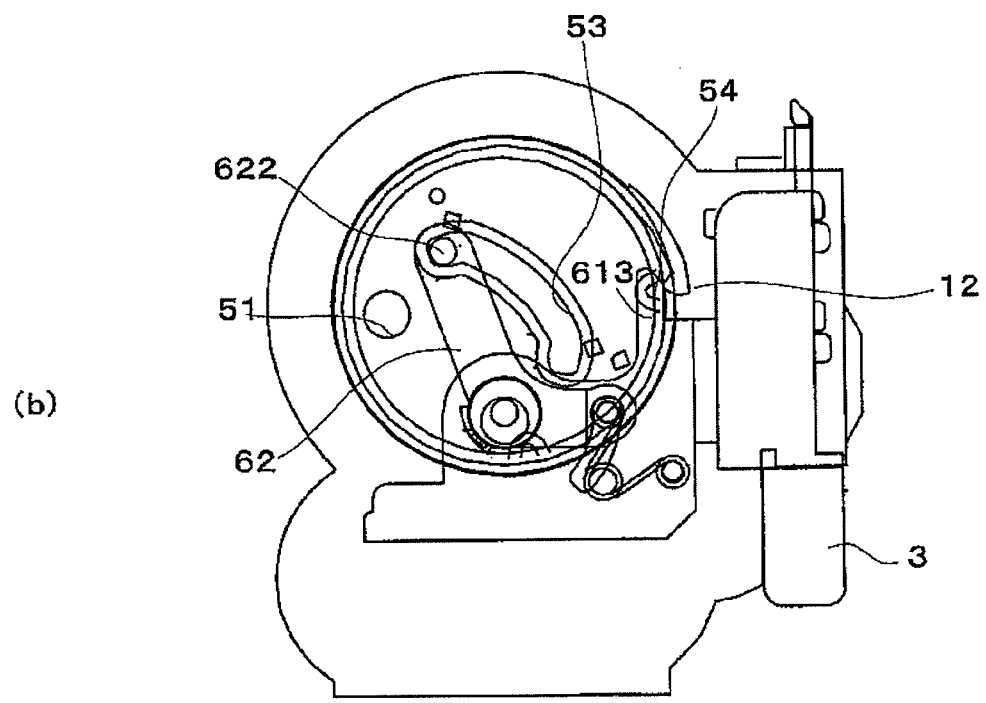
Figure 16:
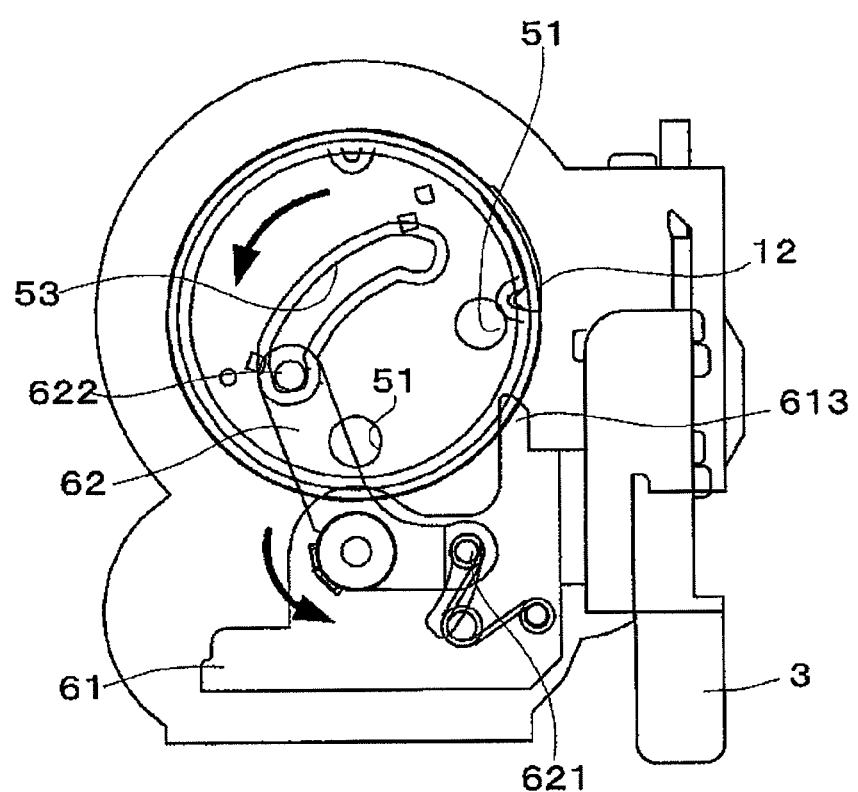
Figure 17:
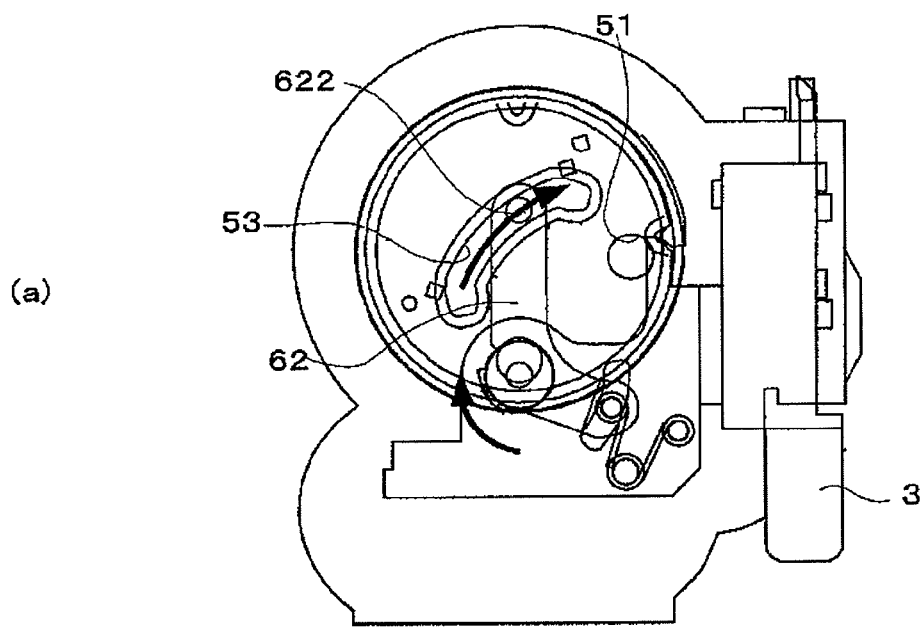
Figure 17:
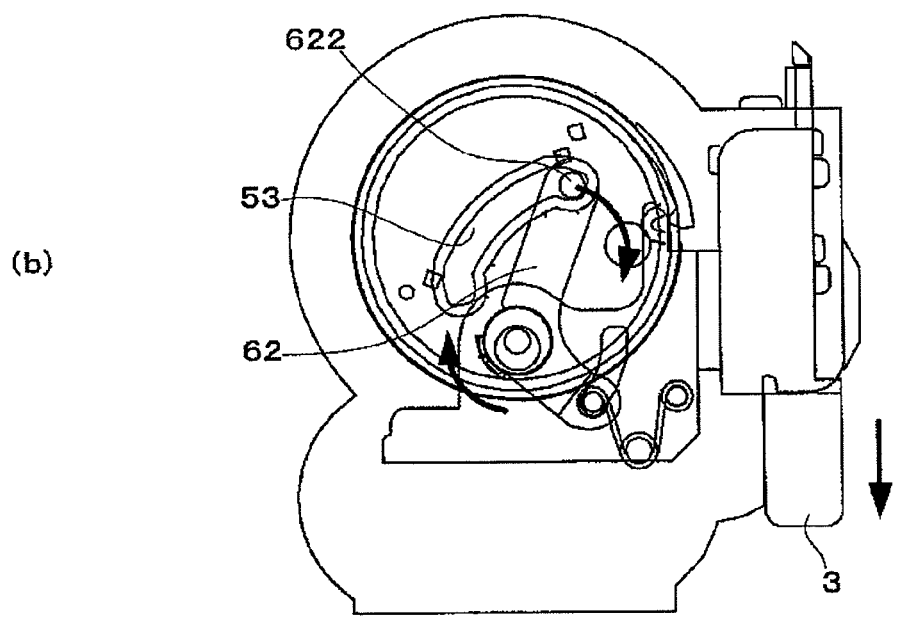

The reciprocal rotation mechanism of the medicament-delivery member is explained below with reference to FIGS. 14 to 17. FIG. 14 is a plan view of the reciprocal rotation mechanism seen from below the medicament-delivery member. FIGS. 15 to 17 are the explanatory views of the operation.

As shown in FIG. 14, a plate-like substrate 61 is uniformly attached on the bottom of the operation button 3. Therefore, the substrate 61 also shifts when the operation button 3 shifts. An L-like driving lever 62 as seen in a plan view is pivotably attached to the substrate 61. A protrusion 621 is provided on one end of the driving lever 62, and the protrusion 621 is pivotably fitted in a circular through-hole 611 formed in the substrate 61. This restricts the pivotable range of the driving lever 62. A spring is provided on one end of the driving lever 62. A protrusion 622 is provided on the other end of the driving lever 62, and the protrusion 622 is engaged in the circular guide groove 53 formed in the bottom of the medicament-delivery member 5. Furthermore, a notch 54 is formed in the circumference of the medicament-delivery member 5. An elastically deformable projected piece 12 formed in the housing 1 is engaged in the notch 54. By being engaged with the projected piece 12, the medicament-delivery member 5 will not rotate when the operation button 3 is depressed. However, as described later, a releasing convex portion 613 projecting toward the projected piece 12 is formed on the substrate 61. When the operation button 3 is depressed, the projected piece 12 is pushed away so that the engagement with the notch 54 is released.

The reciprocal rotation mechanism is explained below with reference to FIGS. 15 to 17. When the operation button 3 is depressed from the initial position shown in FIG. 14, the substrate 61 is also depressed, as shown in FIG. 15(a), and the driving lever 62 pivots accordingly. In this case, the medicament-delivery member 5 does not rotate because it is fixed with the projected piece 12. The protrusion 622 on the other end of the driving lever 62 merely slides along the guide groove 53 in the medicament-delivery member 5. As shown in FIG. 15(b), when the operation button 3 is completely depressed, the releasing convex portion 613 of the substrate 61 pushes the projected piece 12 away so that the engagement between the notch 54 and the projected piece 12 is released. This makes the medicament-delivery member 5 rotatable. The other end of the protrusion 622 of the driving lever 62 is located at one end of the guide groove 53. When the operation button 3 is made to return to the initial position, as shown in FIG. 16, the other end of the protrusion 622 of the driving lever 62 pulls and rotates the medicament-delivery member 5 due to the shift of the operation button 3. This makes one concave portion 51 move from the receiving position to the inhalation position, and the other concave portion 51 move from the inhalation position to the receiving position. When the operation button 3 returns to the initial position, the projected piece 12 in the housing 1 elastically deforms to be re-engaged with another notch 54, so as to fix the medicament-delivery member 5.

Subsequently, when the operation button 3 is further depressed, as shown in FIG. 17(a), the other end of the driving lever 62 moves along the guide groove 53 to the other end of the guide groove 53; however, the medicament-delivery member 5 does not rotate. When the operation button 3 is returned to the initial position, as shown in FIG. 17(b), the other end of the driving lever 62 pulls the other end of the guide groove 53 so as to rotate the medicament-delivery member. As a result, the medicament-delivery member returns to the position shown in FIG. 14. At this time, the rotation progresses, as shown in FIG. 16, in the direction opposite to that made by the previous button operation. As described above, the rotation direction of the medicament-delivery member 5 reverses each time the operation button is depressed; this allows the reciprocal rotation to be performed.

The operation of the powder inhaler having the above structure is summarized below. When a patient needs to inhale the medicament, he/she has to remove the cap 2 to expose the mouthpiece 11 and operation button 3 as the first step. When the operation button 3 is depressed, the stirring member 7 rotates so that the stored medicament is mixed. This prevents blockage due to the medicament. In the process wherein the operation button 3 is returning from the depressed position to the initial position, the concave portion 51 moves from the receiving position toward the inhalation position while receiving the powder medicament. Under this condition, if a patient breathes in while holding the mouthpiece 11 in the mouth, the powder medicament in the concave portion 51 passes through the flow channel S and is then inhaled through the mouthpiece 11.

As described above, in the present embodiment, the housing 1 is provided with a stirring member 7 for stirring the powder medicament, and an operation button 3 that relatively shifts the medicament to the position where the patient can inhale the medicament. While the operation button 3 is being depressed or returning to the initial position, the stirring member can simultaneously be operated. Therefore, the stored powder medicament can be stirred before inhalation, preventing the medicament from being blocked. This makes it possible to store an accurate amount of the medicament in the concave portion 51 and reliably locate the concave portion 51 at the inhalation position.

Second Embodiment

Figure 18:
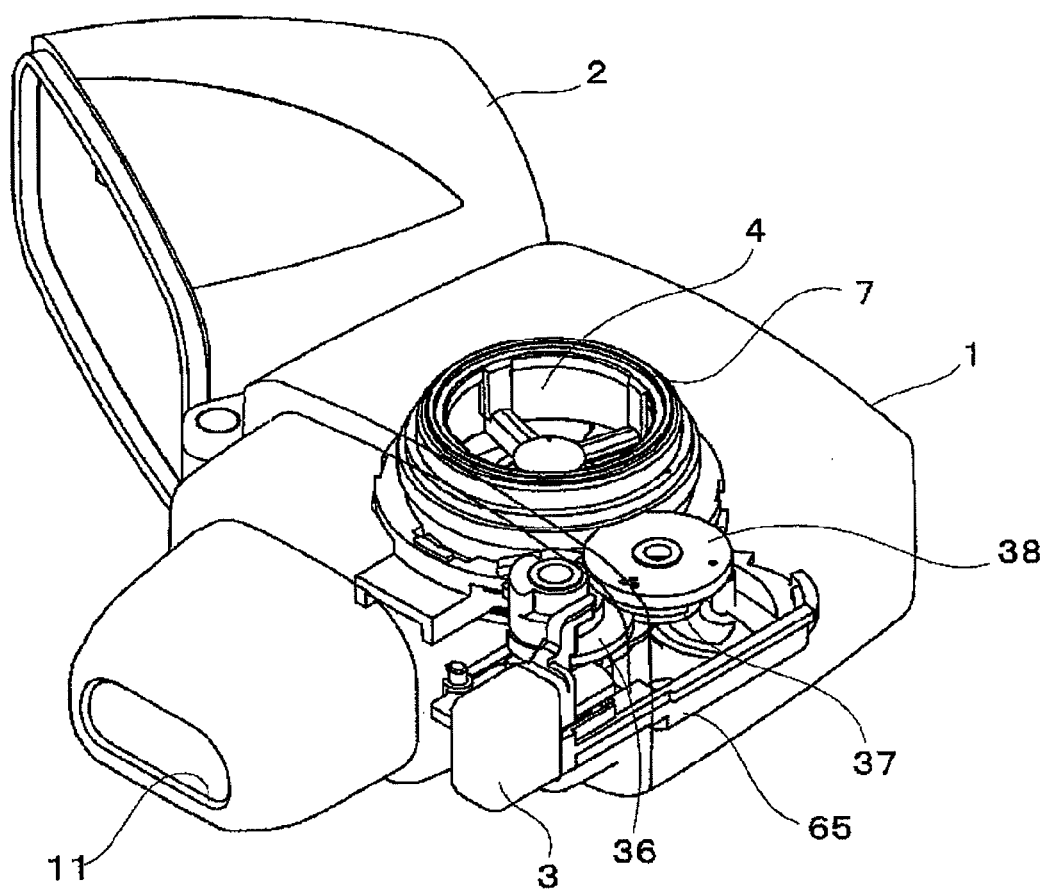
Figure 19:
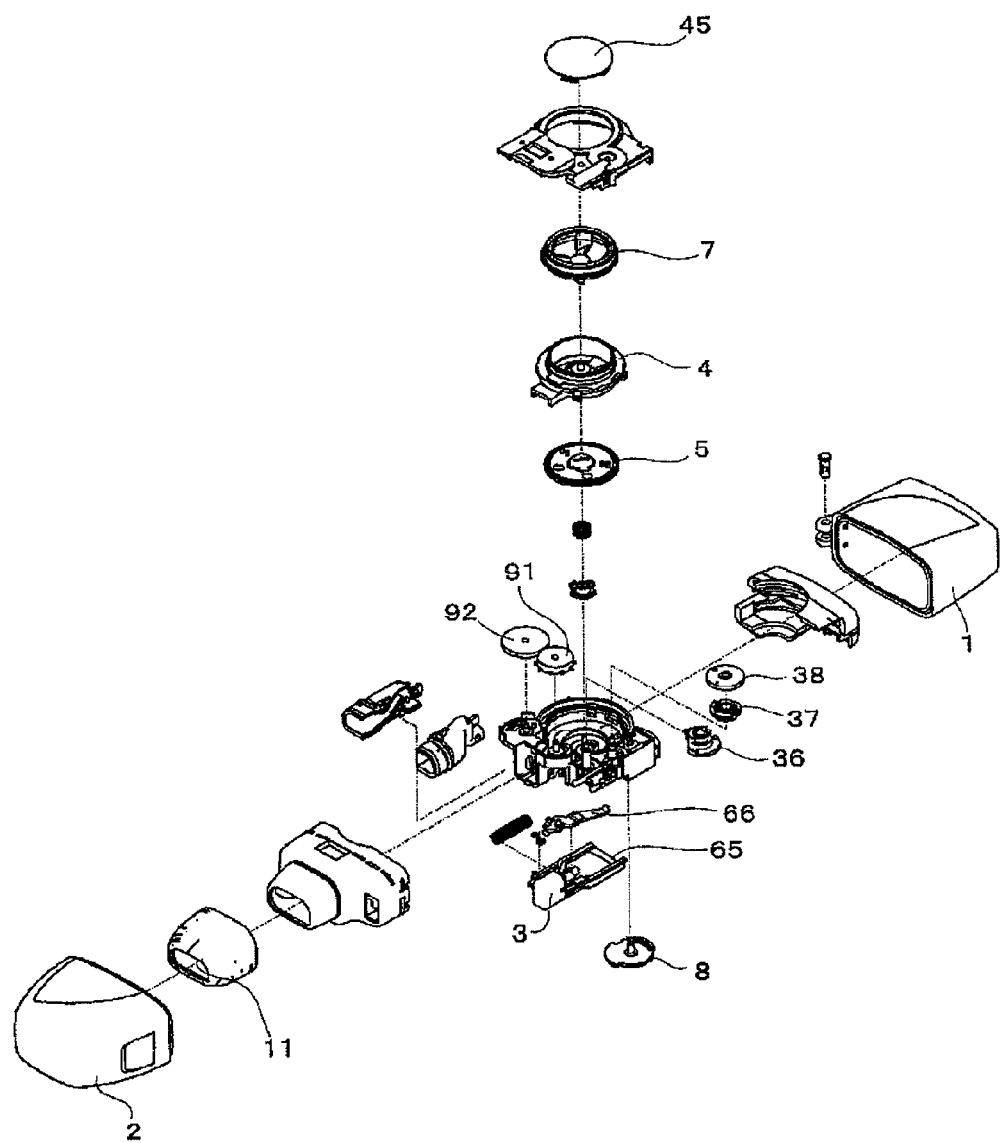
Figure 20:
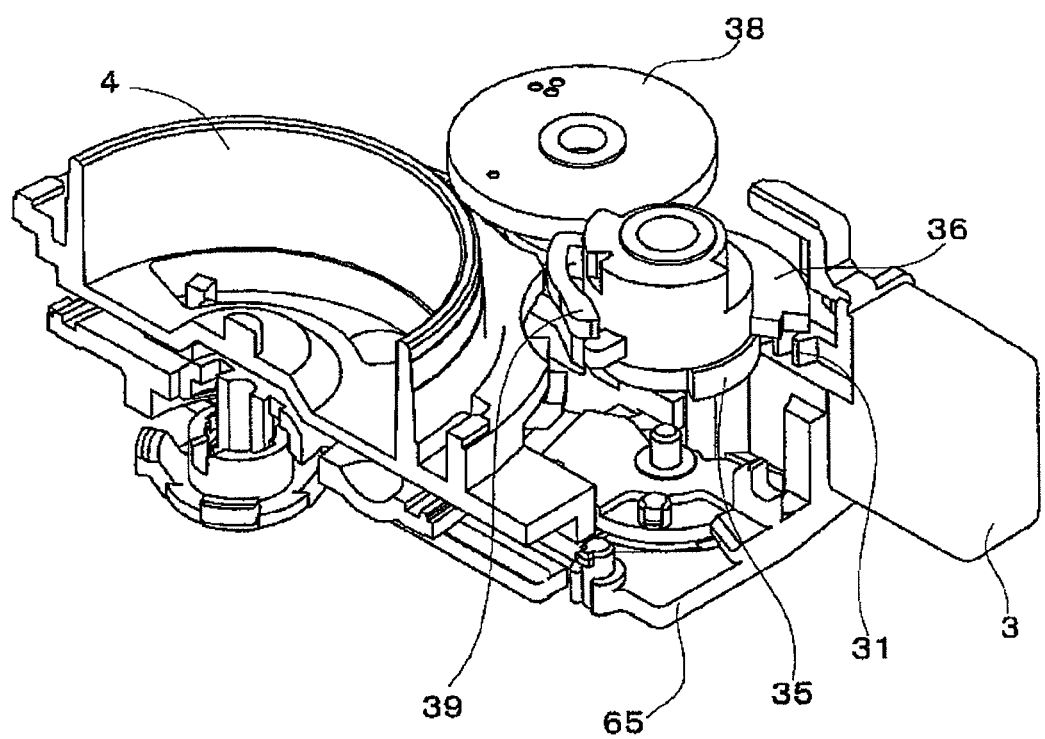
Figure 21:
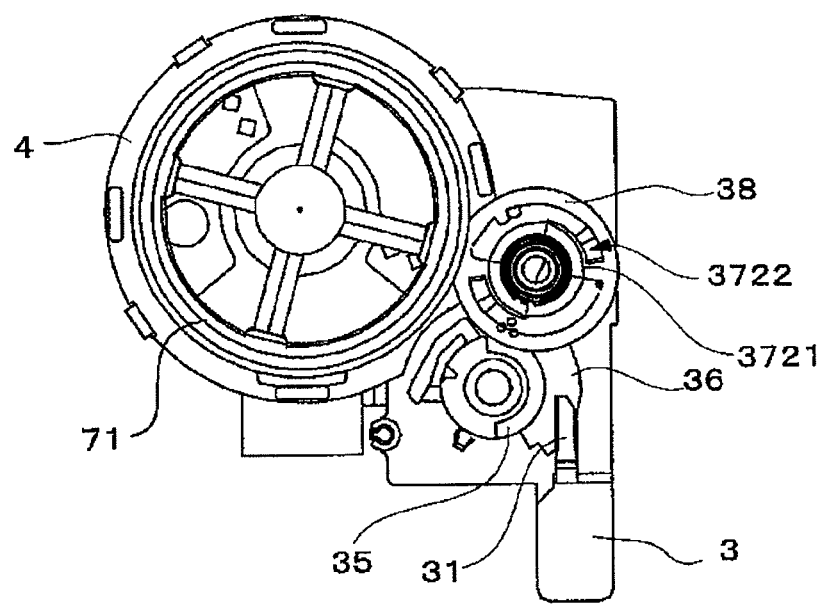
Figure 22:
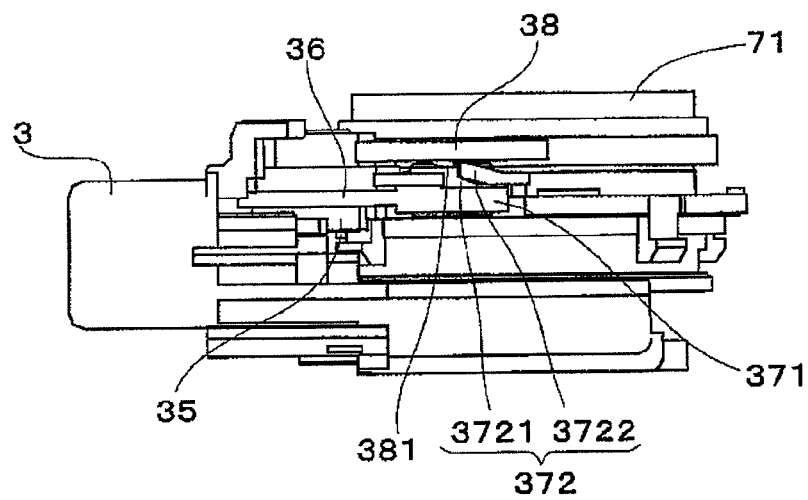
Figure 23:
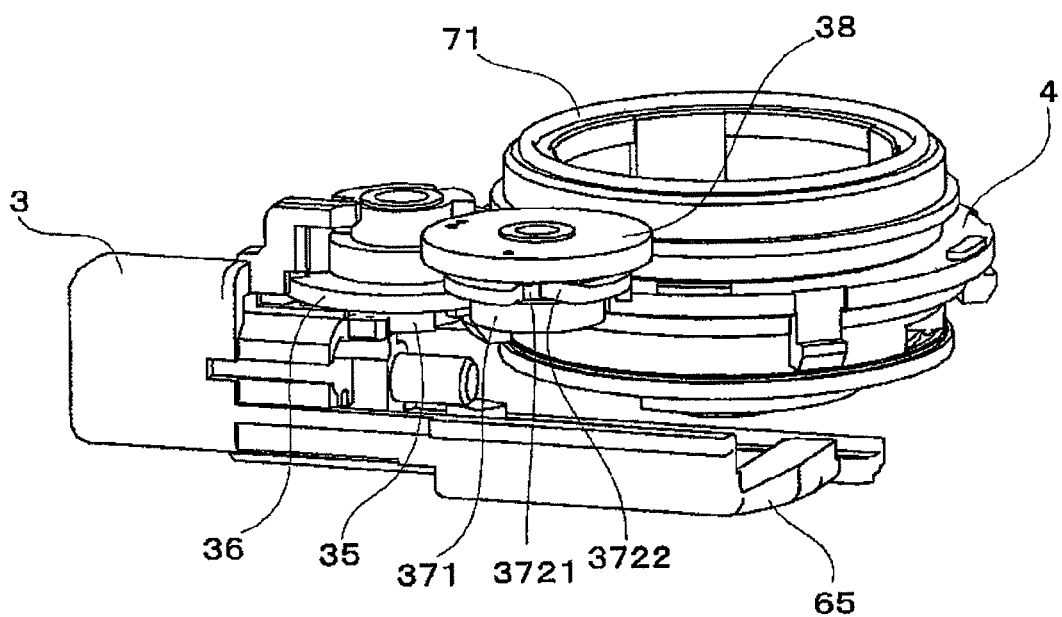

The second embodiment of the powder inhaler of the present invention is explained below with reference to the drawings. The powder inhaler of the second embodiment is different from that of the first embodiment in the driving mechanisms of the stirring member 7, the medicament-delivery member 5, and the counter. Therefore, mainly the mechanisms thereof are explained here, and duplicate explanations of the same structures are omitted. FIG. 18 is a perspective view showing the inner structure of the powder inhaler of this embodiment, FIG. 19 is a perspective exploded view of FIG. 18, FIG. 20 is a partial cutaway perspective view of the storage member of the powder inhaler, FIG. 21 is a plan view of FIG. 20, FIG. 22 is a side view of FIG. 21, and FIG. 23 is a perspective view of FIG. 21.

First, the rotation mechanism of the stirring member 7 is explained. As FIGS. 18 to 23 show, in the same manner as in the first embodiment, the operation button 3 is energized with the spring (not shown) disposed in the housing 1, and a portion of the operation button 3 protrudes from the side surface of the mouthpiece 11 also in the second embodiment. The operation button 3 is provided with a rack 31 in the portion located in the housing 1, wherein the rack 31 meshes with a third gear 35. The third gear 35 is uniformly, coaxially formed with a fourth gear 36 having a larger diameter than the third gear 35. The fourth gear 36 is formed in a fan shape, and rotates uniformly with the third gear 35. The fourth gear 36 also meshes with a fifth gear 37 which is situated behind the fourth gear 36 in the housing 1. A sixth gear 38 is coaxially and rotatably provided on the fifth gear 37. The sixth gear 38 has a larger diameter than the fifth gear 37, and meshes with the gear of an annular frame 71.

The fifth gear 37 has the same structure as the first gear 32 in the first embodiment. Specifically, the fifth gear 37 is formed of a gearing member 371 that meshes with the fourth gear 36, and a circular engaging part 372 that coaxially connects to the gearing member 371 and engages with the sixth gear 38. The engaging part 372 has a shaft member 3721 and two circular engagement pieces 3722 surrounding the outer periphery of the shaft member 3721. Each engagement piece 3722 can elastically deform vertically (to the sixth gear 38 side) and its end in the circumferential direction projects upwardly. The sixth gear 38 also has the same structure as the second gear 33 in the first embodiment. Specifically, the sixth gear 38 is provided with two uniformly formed protrusions 381 that project toward the fifth gear 37. The protrusions 381 can engage with the end of the engagement pieces 3722 in the fifth gear 37.

In this structure, when the operation button 3 reciprocates, the third, fourth and fifth gears 35, 36, and 37 reciprocally rotate. However, in the same manner as the second gear 33 in the first embodiment, the sixth gear 38 rotates in one direction. Accordingly, the annular frame 71 also rotates in one direction. Here, the stirring member 7 rotates in one direction to stir the medicament according to the reciprocating movement of the operation button 3.

Figure 24:
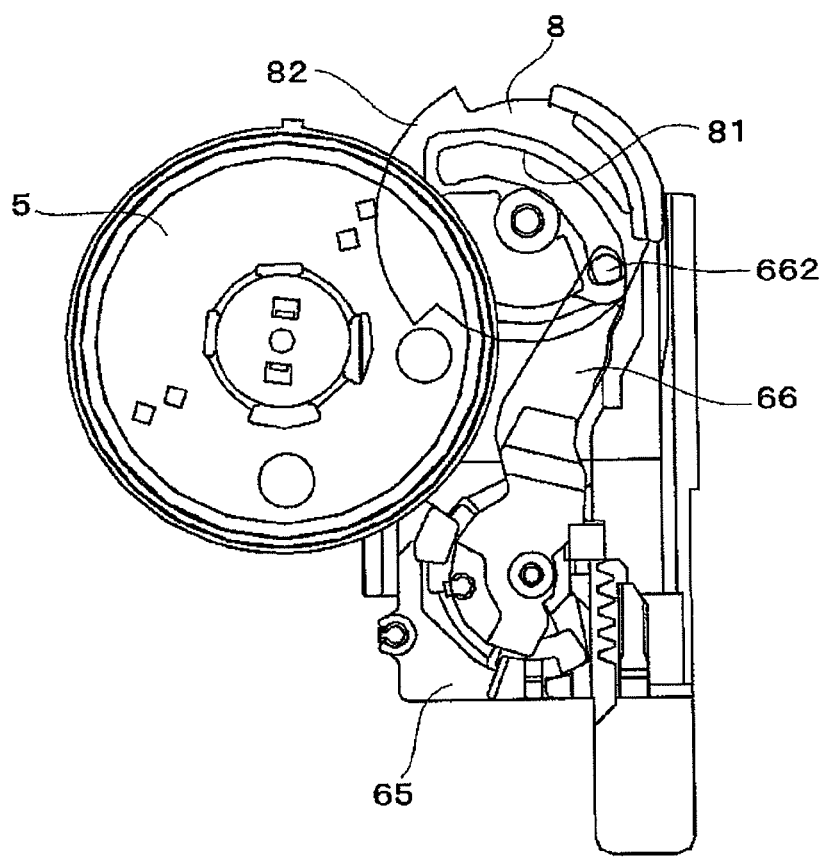

The mechanism for the reciprocal rotation of the medicament-delivery member is explained with reference to FIGS. 24 and 25. FIG. 24 is a plan view showing the inner structure of the powder inhaler, and FIG. 25 is a side view thereof.

Figure 25:
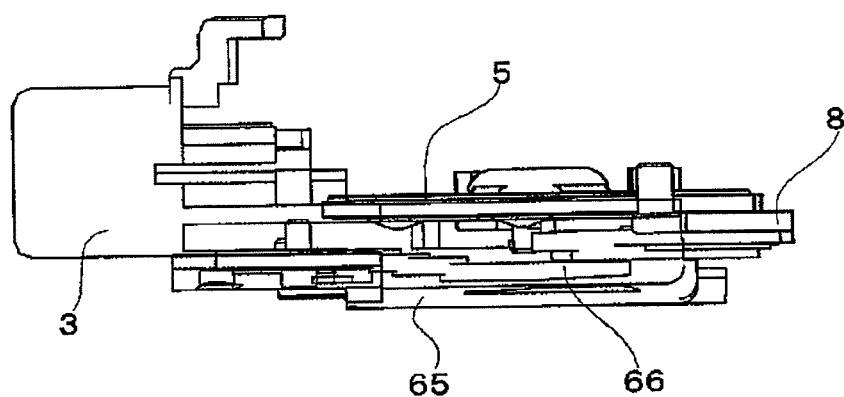

As shown in FIGS. 24 and 25, a plate-like substrate 65 is uniformly attached on the bottom of the operation button 3, wherein the plate-like substrate 65 extends toward the rear end of the housing 1. In the same manner as in the first embodiment, the substrate 65 shifts when the operation button 3 shifts. A linearly extending driving lever 66 is pivotably attached to the substrate 65. A spring (not shown) is provided on the mouthpiece-side end of the driving lever 66. On the other end of the driving lever 66, a protrusion 662 is provided. The protrusion 662 engages with a rotatable lever 8 located in the rear section of the housing 1. The rotatable lever 8 is formed into a disc-like shape and rotatably supported in the housing 1. A circular guide hole 81, in which a protrusion 662 of the driving lever 66 engages, is formed in the surface of the rotatable lever 8.

Gear teeth 82 are formed on the part of the side surface of the rotatable lever 8. The gear teeth are formed on the surface facing to the medicament-delivery member 5, and mesh with the gear teeth formed on the bottom of the medicament-delivery member 5. Therefore, the medicament-delivery member 5 can rotates in accordance with the rotation of the rotatable lever 8.

As described above, the reciprocating movement of the operation button 3 in the second embodiment makes it possible, in the same manner as shown in FIGS. 14 to 16, to reverse the rotation direction of the medicament-delivery member 5 each time the operation button 3 is depressed; this allows reciprocal rotation to be performed.

In particular, a rotatable lever 8 having a guide hole 81 is additionally provided in the second embodiment. The rotatable lever 8 can generate the power transmission to the medicament-delivery member 5 on the same surface as much as possible to eliminate the torsion while the medicament-delivery member 5 moves, thereby the power loss due to friction can be reduced compared with the first embodiment. In addition, the length from the supporting point of the driving lever 66 to the protrusion 662 is extended compared to that in the first embodiment. This reduces the pivot angle of the driving lever 66 and then the power loss can be reduced. Accordingly, the force necessary to make the driving lever 66 pivot is efficiently transmitted, and the medicament-delivery member 5 can be rotated with less force.

Figure 26:
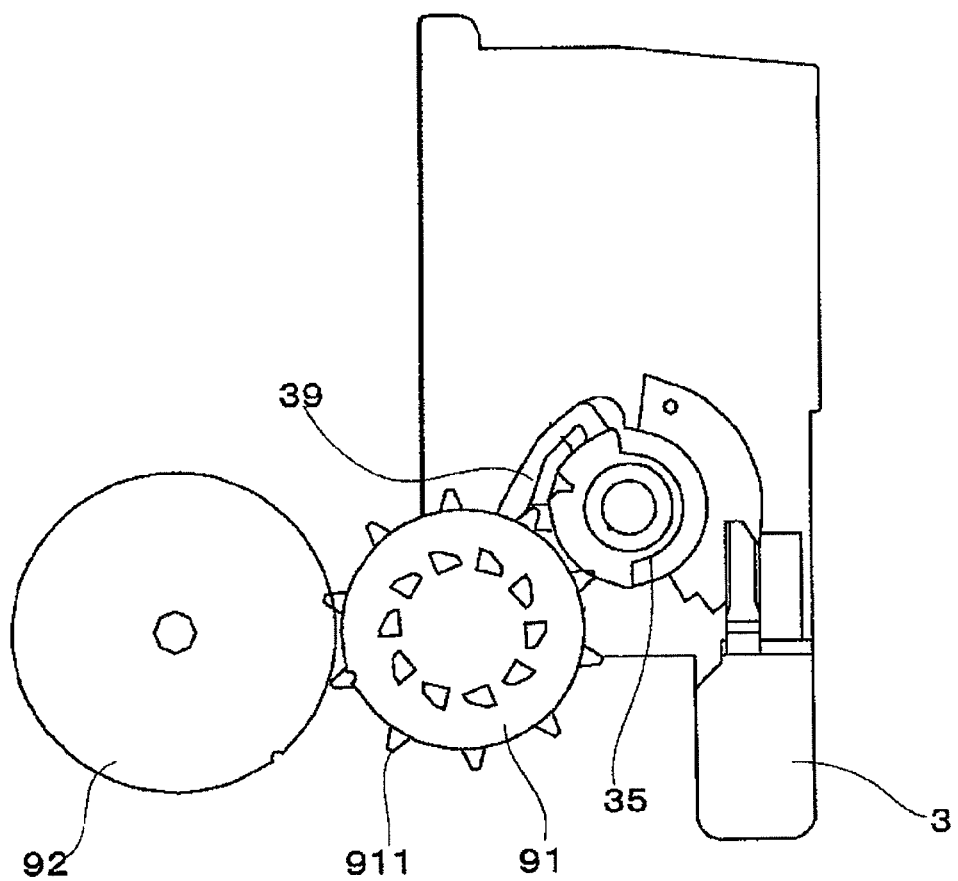
Figure 27:
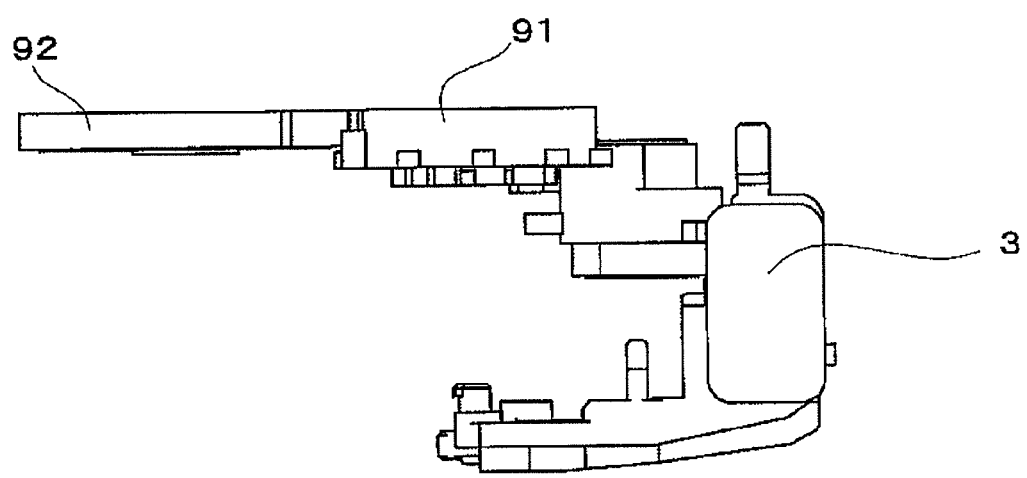

The driving mechanism of the counter is explained with reference to FIGS. 26 and 27. FIG. 26 is a plan view showing the inner structure of the powder inhaler, and FIG. 27 is a side view of the powder inhaler from the mouthpiece shown in FIG. 26. As shown in FIGS. 26 and 27, the counter includes a disc-like first counting member 91 on which the figures in the ones place are printed and a disc-like second counting member 92 on which the figures in the tens and hundreds place are printed. On the surfaces of the first counting members 91, the figures from 0 to 9 are printed along the circumferential direction. On the surfaces of the second counting members 92, for example, the figures from 1 to 20 are printed along the circumferential direction. Accordingly, the counter can count 1 to 200. However, the figures in the counter are not limited to this embodiment, for example, the counter may count from the maximum indicated figure. These figures appear through the window of the housing, indicating the remaining number of usable times. These counting members 91 and 92 have gears on their outer peripheries. The gear ratio between the counting members 91 and 92 is set so that when the first counting member 91 makes one rotation, the figure appearing on the second counting member 92 decreases by one. In this structure, an engagement piece 39 provided uniformly with the third gear 35 engages with a projection 911 formed on the periphery of the first counting member 91. The engagement piece 39 is almost the same as that provided to the fifth gear 37, wherein the first counting member 91 is designed to rotate only in one direction even when the engagement piece 39 reciprocally rotates by the reciprocating movement of the operation button 3. The first counting member 91 is deigned to rotate in one direction via the engagement piece 39 when the operation button 3 is depressed. Thus, the figure in the ones place is counted down. When the first counting member 91 makes one rotation, the second counting member 92 rotates by a predetermined angle, and the figure in the tens place or the hundreds place is decreased by one; thus indicating the remaining number of usable times.

As described above, in the same manner as in the first embodiment, the powder inhaler in the second embodiment is also structured so that the stirring member 7 is concurrently operated when the operation button 3 is depressed or returns to the initial position. This structure allows the stored medicament to be stirred before inhalation, preventing the medicament from coagulating.

Two embodiments of the present invention are explained above; however, the scope of the present invention is not limited to the above embodiment and can be modified as long as it does not depart from the intention of the present invention. For example, in the above embodiment, the powder medicament is mixed by four stick-like impellers 73, but instead of the impellers 73 or in addition to the impellers 73, a screw-type impeller may be used to further improve the stirring efficiency. The number of the impellers can be increased. Accordingly, the number of the impellers passing over the exhaust port in one operation can be increased, improving the stirring efficiency. In other words, there is no limitation to the shape and the number of the impeller, and the selection thereof can be suitably made depending on the properties of the medicament.

It is preferable that the impellers 73 be located in the vicinity of the medicament-delivery member 5 in the storage member 4. In this arrangement, the medicament that is placed near the medicament-delivery member 5 in the storage member 4 is delivered to the medicament-delivery member 5 through exhaust port 41 while being stirred.

Figure 3:
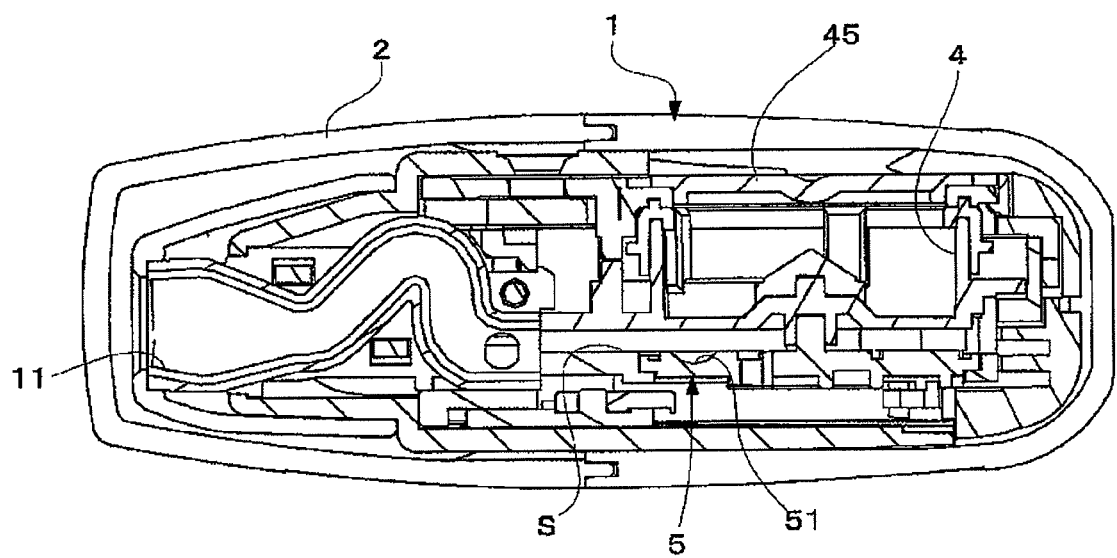

If the stirring member 7 is provided with four stick-like impellers as in the above embodiment, by making a hopper cap 45 (see FIGS. 3 and 19) covering the storage member 4 relatively thick so as to adjust the volume of the storage member, stirring and delivering the medicament to the concave portion 51 of the medicament-delivery member 5 at the receiving position can be conducted more smoothly.

The counter explained above displays figures, but the other type of the counter, for example an indicator displaying the amount of the remaining amount of the medicament, can be used. Further, a desiccant agent may be provided in the housing.

Additives providing electric conduction (for example, an electric conduction filler such as carbon or chemical compound) may be given to the materials of the medicament-delivery member, the storage member, the stirring member, the gears, and the mouthpiece which contact medicament or other members to provide them with electric conduction so as to induce electrostatic leakage. Note that, such electric conduction may also be given to the other members.

EXPLANATION OF REFERENCE NUMERALS

1 Housing
3 Operation button
4 Storage member
41 Exhaust port
5 Medicament-delivery member
51 Concave Portion
52 Protrusion
7 Stirring Member

The invention claimed is:

1. A powder inhaler comprising:
a housing having an admission port;
a storage member provided in the housing for storing a powder medicament;
a medicament-delivery member provided in the housing, the medicament-delivery member comprising at least one concave portion for receiving a predetermined amount of the powder medicament, said at least one concave portion being capable of moving into, relative to the storage member, a receiving position in which the at least one concave portion receives the predetermined amount of powder medicament from the storage member, and an inhalation position in which the powder medicament can be inhaled through the admission port;
a stirring member rotatably provided in the storage member for stirring the powder medicament stored in the storage member by the rotation thereof; and
an operation button provided in the housing and being capable of moving between an initial position and a depressed position,
while the operation button reciprocates between the initial position and the depressed position, the at least one concave portion in the medicament-delivery member moves from the receiving position to the inhalation position and the stirring member operates,
wherein the shift of the operation button from the initial position to the depressed position causes the stirring member to rotate, and the shift of the operation button from the depressed position to the initial position causes the at least one concave portion in the medicament-delivery member to move from the receiving position to the inhalation position.

2. The powder inhaler according to claim 1, wherein the storage member comprises an exhaust port from which the powder medicament is discharged, a region including the at least one concave portion of the medicament-delivery member is formed so as to cover the exhaust port at the receiving position, and, while the at least one concave portion moves, in a relative manner, from the receiving position to the inhalation position, an inner wall of the exhaust port removes the powder medicament that overflows from the at least one concave portion.

3. The powder inhaler according to claim 2, wherein the medicament-delivery member comprises a protrusion projecting toward the exhaust port, and the protrusion follows the at least one concave portion while the medicament-delivery member moves.

4. The powder inhaler according to claim 1, wherein the stifling member comprises a rotational shaft, and a plurality of impellers radially extending from the rotational shaft.

5. The powder inhaler according to claim 2, wherein the stifling member comprises a rotational shaft and a plurality of impellers radially extending from the rotational shaft, wherein at least one of the impellers is structured so as to move to the region corresponding to the exhaust port.

6. The powder inhaler according to claim 1, wherein the medicament-delivery member reciprocates, relative to the storage member, between the receiving position and the inhalation position.

7. The powder inhaler according to claim 1, wherein the medicament-delivery member moves between the receiving position and the inhalation position while rotating in one direction relative to the storage member.

* * * * *